United States Patent
Weichert et al.

[11] Patent Number: 5,869,531
[45] Date of Patent: Feb. 9, 1999

[54] FLUOROALKYL SUBSTITUTED BENZOYLGUANIDINES

[75] Inventors: Andreas Weichert, Egelsbach; Heinz-Werner Kleemann, Bischofsheim; Hans-Jochen Lang, Hofheim; Jan-Robert Schwark, Frankfurt; Udo Albus, Florstadt; Wolfgang Scholz, Eschborn, all of Germany

[73] Assignee: Hoechst Aktiengesellschaft, Frankfurt am Main, Germany

[21] Appl. No.: 525,095

[22] Filed: Sep. 8, 1995

[30] Foreign Application Priority Data

Sep. 9, 1994 [DE] Germany .................. 44 32 105.8

[51] Int. Cl.⁶ .......... A61K 31/155; C07C 233/64; C07C 279/02
[52] U.S. Cl. .......... 514/618; 514/634; 564/162; 564/183; 564/230
[58] Field of Search ................ 564/162, 183, 564/230; 514/618, 634

[56] References Cited

U.S. PATENT DOCUMENTS

| 3,780,027 | 12/1973 | Cragoe, Jr. et al. |
| 5,091,394 | 2/1992 | Englert et al. ................ 564/85 |
| 5,373,024 | 12/1994 | Lang et al. .................. 514/618 |

FOREIGN PATENT DOCUMENTS

| B-55229 | 8/1994 | Australia . |
| A-602-522 | 6/1994 | European Pat. Off. . |
| A-604-852 | 7/1994 | European Pat. Off. . |

*Primary Examiner*—José G. Dees
*Assistant Examiner*—Barbara Badio
*Attorney, Agent, or Firm*—Finnegan, Henderson, Farabow, Garrett & Dunner, L.L.P.

[57] ABSTRACT

Disclosed are 4-(2'-trifluoromethylethyl)benzoylguanidine and 3-methylsulfonyl-4-(2'-trifluoromethylethyl) benzoylguanidine. Also disclosed are pharmaceutical compositions and the use of the compounds in the treatment of disorders induced by ischemia.

3 Claims, No Drawings

FLUOROALKYL SUBSTITUTED BENZOYLGUANIDINES

The invention relates to benzoylguanidines of the formula I $$\text{[Structure I: benzene ring with R(1), R(2), R(3), R(4) substituents and a C(=O)-N=C(NH}_2\text{)NH}_2\text{ group]}$$

in which:
R(1) is hydrogen, F, Cl, Br, I, CN, NO$_2$, OH, (C$_1$–C$_8$)-alkyl, (C$_3$–C$_8$)-cycloalkyl, O$_a$—(CH$_2$)$_b$—(CF$_2$)$_c$—CF$_3$;
a is zero or 1;
b is zero, 1 or 2;
c is zero, 1, 2 or 3; or
R(1) R(5)—SO$_m$ or R(6)R(7)N—SO$_2$—;
m is zero, 1 or 2;
R(5) and R(6) independently of one another are (C$_1$–C$_8$)-alkyl, (C$_3$–C$_6$)-alkenyl, CF$_3$ or —C$_n$H$_{2n}$—R(8);
n is zero, 1, 2, 3 or 4;
R(7) is hydrogen or (C$_1$–C$_4$)-alkyl;
R(8) is (C$_3$–C$_7$)-cycloalkyl or phenyl,
which is not substituted or is substituted by 1–3 substituents selected from the group consisting of F, Cl, CF$_3$, methyl, methoxy and NR(9)R(10);
R(9) and R(10) independently of one another are hydrogen or (C$_1$–C$_4$)-alkyl; or
R(6) is H;
or R(6) and R(7)
together are 4 or 5 methylene groups, of which one CH$_2$ group can be replaced by oxygen, S, NH, N—CH$_3$ or N-benzyl, or
R(1) is —SR(11), —OR(11) or —CR(11)R(12)R(13);
R(11) is —C$_p$H$_{2p}$—(C$_3$–C$_8$)-cycloalkyl, —(C$_1$–C$_9$)-heteroaryl or phenyl,
the aromatic systems being unsubstituted or substituted by 1–3 substituents selected from the group consisting of F, Cl, CF$_3$, CH$_3$, methoxy, hydroxyl, amino, methylamino and dimethylamino;
R(12) and R(13) independently of one another are defined as R(11) or are hydrogen or (C$_1$–C$_4$)-alkyl;
p is zero, 1 or 2; or
R(1) is phenyl, naphthyl, biphenylyl or (C$_1$–C$_9$)-heteroaryl, the latter linked via C or N,
which are unsubstituted or substituted by 1–3 substituents selected from the group consisting of F, Cl, CF$_3$, CH$_3$, methoxy, hydroxyl, amino, methylamino and dimethylamino;
R(2) is —CF$_2$R(14), —CF[R(15)] [R(16)], —CF[(CF$_2$)$_q$—CF$_3$)]-[R(15)], —C[(CF$_2$)$_r$—CF$_3$]=CR(15)R(16);
R(14) is (C$_1$–C$_4$)-alkyl or (C$_3$–C$_6$)-cycloalkyl;
R(15) and R(16) independently of one another are hydrogen or (C$_1$–C$_4$)-alkyl;
q is zero, 1 or 2;
r is zero, 1 or 2;
R(3) is defined as R(1);
R(4) is hydrogen, (C$_1$–C$_3$)-alkyl, F, Cl, Br, I, CN or —(CH$_2$)$_s$—(CF$_2$)$_t$—CF$_3$;
s is zero or 1;
t is zero, 1 or 2;
and their pharmaceutically tolerable salts.

Preferred compounds of the formula I are those in which:
R(1) is H, F, Cl, Br, CN, (C$_1$–C$_4$)-alkyl, (C$_3$–C$_6$)-cycloalkyl, O$_a$—(CF$_2$)$_c$—CF$_3$;
a is zero or 1;
C is zero, 1, 2 or 3; or
R(1) is R(5) —SO$_m$ or R(6)R(7)N—SO$_2$—;
m is zero, 1 or 2;
R(5) and (R6) independently of one another are (C$_1$–C$_4$)-alkyl, (C$_3$–C$_6$)-alkenyl, CF$_3$ or —C$_n$H$_{2n}$—R(8);
n is zero or 1;
R(7) is hydrogen or (C$_1$–C$_4$)-alkyl;
R(8) is (C$_3$–C$_6$)-cycloalkyl or phenyl,
which is unsubstituted or substituted by 1–3 substituents selected from the group consisting of F, Cl, CF$_3$, methyl, methoxy and NR(9)R(10);
R(9) and R(10) are hydrogen or (C$_1$–C$_4$)-alkyl; or
R(6) is hydrogen; or
R(6) and R(7)
together are 4 or 5 methylene groups, of which one CH$_2$ group can be replaced by oxygen, S, NH, N—CH$_3$ or N-benzyl, or
R(1) is —OR(11);
R(11) is —C$_f$H$_{2f}$—(C$_3$–C$_6$)-cycloalkyl, —(C$_1$–C$_9$)-heteroaryl or phenyl,
the aromatic systems being unsubstituted or substituted by 1–3 substituents selected from the group consisting of F, Cl, CF$_3$, CH$_3$, methoxy, hydroxyl, amino, methylamino and dimethylamino;
f is zero or 1; or
R(1) is phenyl, naphthyl, biphenylyl or (C$_1$–C$_9$)-heteroaryl, the latter linked via C or N,
and which are unsubstituted or substituted by 1–3 substituents selected from the group consisting of F, Cl, CF$_3$, CH$_3$, methoxy, hydroxyl, amino, methylamino and dimethylamino;
R (2) is —CF$_2$R(14), —CF[R(15)] [R(16)], —CF[(CF$_2$)$_q$—CF$_3$)]-[R(15)], —C[(CF$_2$)$_r$—CF$_3$]=CR(15)R(16);
R(14) is (C$_1$–C$_4$)-alkyl or (C$_3$–C$_6$)-cycloalkyl;
R(15) and R(16)
independently of one another are hydrogen or (C$_1$–C$_4$) alkyl;
q is zero, 1 or 2;
r is zero, 1 or 2;
R(3) is defined as R(1);
R(4) is H, (C$_1$–C$_3$)-alkyl, F, Cl, Br, CN or CF$_3$;
and their pharmaceutically tolerable salts.

Particularly preferred compounds of the formula I are those in which:
R(1) is hydrogen, F, Cl, Br, (C$_1$–C$_4$)-alkyl, (C$_5$–C$_6$)-cycloalkyl, O$_a$—(CF$_2$)$_c$—CF$_3$;
a is zero or 1;
c is zero or 1; or
R(1) is R(5)—SO$_2$;
R(5) is (C$_1$–C$_4$)-alkyl or CF$_3$; or
R(1) is —OR(11);
R(11) is
(C$_4$–C$_6$)-cycloalkyl, quinolyl, isoquinolyl, pyridyl, in each case bonded via C or N, or phenyl,
which is unsubstituted or substituted by 1–3 substituents selected from the group consisting of F, Cl, CF$_3$, CH$_3$, methoxy, hydroxyl, amino, methylamino and dimethylamino; or R(1) is quinolyl, isoquinolyl, pyridyl, in each case bonded via C or N, or phenyl,
which is unsubstituted or substituted by 1–3 substituents selected from the group consisting of F, Cl, CF$_3$, CH$_3$, methoxy, hydroxyl, amino, methylamino and dimethylamino;

R(2) is —CF$_2$R(14), —CF[R(15)] [R(16)], —CF(CF$_3$) [R(15)], —C(CF$_3$)=CR(15)R(16);

R(14) is (C$_1$–C$_4$)-alkyl or (C$_3$–C$_6$)-cycloalkyl;

R(15) and R(16)
independently of one another are hydrogen or (C$_1$–C$_4$)-alkyl;

R(3) is hydrogen, F, Cl, Br, I, —SO$_2$Me or CF$_3$;

R(4) is hydrogen, methyl, F, Cl or —CF$_3$;

and their pharmaceutically tolerable salts.

(C$_1$–C$_9$)-Heteroaryl is understood as meaning radicals which are derived from phenyl or naphthyl, in which one or more CH groups are replaced by N and/or in which at least two adjacent CH groups (with formation of a five-membered aromatic ring) are replaced by S, NH or O. In addition, one or both atoms of the condensation site of bicyclic radicals (such as in indolizinyl) can also be N atoms.

(C$_1$–C$_9$)-Heteroaryl includes, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoguinolyl, phthalazinyl, quinoxalinyl, quinazolinyl, cinnolinyl.

If one of the substituents R(1) to R(4) contains one or more centers of asymmetry, these can have either the S or R configuration. The compounds can be present as optical isomers, as diastereomers, as racemates or as mixtures thereof.

The designated alkyl radicals can be either straight-chain or branched.

The invention furthermore relates to a process for the preparation of the compound I which comprises reacting a compound of the formula II

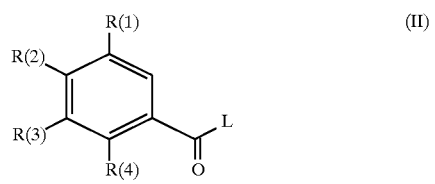

in which R(1) to R(4) have the meaning indicated and L is a leaving group which can readily be substituted nucleophilically, with guanidine.

The activated acid derivatives of the formula II in which L is an alkoxy group, preferably a methoxy group, a phenoxy group, phenylthio, methylthio or 2-pyridylthio group, or a nitrogen heterocycle, preferably 1-imidazolyl, are advantageously obtained in a manner known per se from the underlying carbonyl chlorides (formula II, L=Cl), which for their part can in turn be prepared in a manner known per se from the underlying carboxylic acids (formula II, L=OH), for example using thionyl chloride.

Besides the carbonyl chlorides of the formula II (L=Cl), further activated acid derivatives of the formula II can be prepared in a manner known per se directly from the underlying benzoic acid derivatives (formula II, L=OH), for example the methyl esters of the formula II where L=OCH$_3$ by treatment with gaseous HCl in methanol, the imadazolides of the formula II by treatment with carbonyldiimidazole [L=1=imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, and also the activation of benzoic acids with dicyclohexyl-carbodiimide (DCC) or with O-[(cyano(ethoxycarbonyl)-methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are indicated under details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. In this case, in the reaction of the methyl benzoates (II, L=OMe) with guanidine, methanol, isopropanol or THF from 20° C. to the boiling point of these solvents have proven suitable. In most reactions of compounds II with salt-free guanidine, the reaction was advantageously carried out in aprotic inert solvents such as THF, dimethoxyethane or dioxane. However, water can also be used as a solvent in the reaction of II with guanidine when using a base such as, for example, NaOH.

If L=Cl, the reaction is advantageously carried out with addition of an acid scavenger, e.g. in the form of excess guanidine for binding the halohydric acid.

Some of the underlying benzoic acid derivatives of the formula II are known and described in the literature. The unknown compounds of the formula II can be prepared by methods known from the literature. The benzoic acids obtained are reacted by one of the process variants described above to give the compounds I according to the invention.

The introduction of some substituents in the 2-, 3-, 4- and 5-position takes place by literature-known methods of palladium-mediated cross-coupling of aryl halides or aryl triflates with, for example, organostannanes, organoboronic acids or organoboranes or organocopper or organozinc compounds.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methylsulfonates and p-toluenesulfonates.

The compounds I are substituted acylguanidines.

The most prominent representative of the acylguanidines is the pyrazine derivative amiloride, which is used as a potassium-sparing diuretic in therapy. Numerous other compounds of the amiloride type are described in the literature, such as, for example, dimethylamiloride or ethylisopropylamiloride.

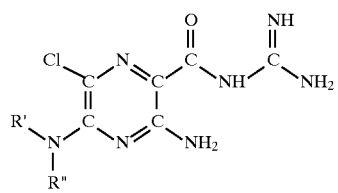

Amiloride: R', R"=H
Dimethylamiloride: R', R"=CH$_3$
Ethylisopropylamiloride: R'=C$_2$H$_5$, R"=CH(CH$_3$)$_2$ Moreover, investigations have been disclosed which point to antiarrhythmic properties of amiloride (Circulation 79, 1257–63 (1989)). Wide application as an antiarrhythmic is opposed, however, by the fact that this effect is only slightly pronounced and occurs accompanied by a hypotensive and saluretic action and these side effects are undesirable in the treatment of cardiac arrhythmias.

Information on antiarrhythmic properties of amiloride was also obtained in experiments on isolated animal hearts (Eur. Heart J. 9 (suppl. 1): 167 (1988) (book of abstracts)). It was thus found, for example on rat hearts, that it was possible completely to suppress an artificially induced ventricular fibrillation by means of amiloride. Even more potent than amiloride in this model was the abovementioned amiloride derivative ethylisopropylamiloride.

U.S. Pat. No. 5,091,394 and European Offenlegungsschrift 0 556 674 A1 (HOE 92/F 034), describe benzoylguanidines which, however, do not have any (partly) fluorinated alkyl or alkenyl side chains for metabolic stabilization.

U.S. Pat. No. 3,780,027 claims acylguanidines which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties, such as occur, for example, in the case of oxygen deficiency symptoms. On account of their pharmacological properties, the compounds are outstandingly suitable as antiarrhythmic pharmaceuticals having a cardioprotective component for infarct prophylaxis and infarct treatment and for the treatment of angina pectoris, where they also inhibit or greatly decrease in a preventive manner the pathophysiological processes in the formation of ischemically induced damage, in particular in the elicitation of ischemically induced cardiac arrhythmias. Because of their protective effects against pathological hypoxic and ischemic situations, the compounds of the formula I according to the invention can be used, on account of inhibition of the cellular $Na^+/H^+$ exchange mechanism, as pharmaceuticals for the treatment of all acute or chronic damage induced by ischemia or diseases primarily or secondarily induced thereby. This relates to their use as pharmaceuticals for surgical interventions, e.g. in organ transplant, where the compounds can be used both for the protection of the organs in a donor before and during removal, for the protection of removed organs, for example during treatment with or storage thereof in physiological bath fluids, and also in the transfer to the body of the recipient. The compounds are also useful pharmaceuticals having a protective effect when carrying out angioplastic surgical interventions, for example on the heart, and also in peripheral vessels. In accordance with their protective effect against ischemically induced damage, the compounds are also suitable as pharmaceuticals for the treatment of ischemias of the nervous system, in particular of the CNS, where they are suitable e.g. for the treatment of stroke or of cerebral edema. Moreover, the compounds of the formula I according to the invention are also suitable for the treatment of forms of shock, such as, for example, of allergic, cardiogenic, hypovolemic and bacterial shock.

Moreover, the compounds of the formula I according to the invention are distinguished by potent inhibiting action on the proliferation of cells, for example of fibroblast cell proliferation and of the proliferation of the vascular smooth muscle cells. The compounds of the formula I are therefore suitable as useful therapeutics for diseases in which cell proliferation is a primary or secondary cause, and can therefore be used as antiatherosclerotics, agents against diabetic late complications, carcinoses, fibrotic disorders such as pulmonary fibrosis, liver fibrosis or kidney fibrosis, organ hypertrophies and hyperplasias, in particular in prostate hyperplasia or prostate hypertrophy.

The compounds according to the invention are effective inhibitors of the cellular sodium-proton antiporter ($Na^+/H^+$ exchanger), which in numerous disorders (essential hypertension, atherosclerosis, diabetes etc.) is also raised in those cells which are readily accessible to measurements, such as, for example, in erythrocytes, platelets or leukocytes. The compounds according to the invention are therefore suitable as outstanding and simple scientific tools, for example in their use as diagnostics for the determination and differentiation of certain forms of hypertension, but also of atherosclerosis, diabetes, proliferative disorders etc. Moreover, the compounds of the formula I are suitable for preventive therapy for preventing the genesis of high blood pressure, for example of essential hypertension.

In this connection, pharmaceuticals which contain a compound I can be administered orally, parenterally, intravenously, rectally or by inhalation, the preferred administration being dependent on the particular symptoms of the disorder. In this connection, the compounds I can be used on their own or together with pharmaceutical auxiliaries, and in fact both in veterinary and in human medicine.

The auxiliaries which are suitable for the desired pharmaceutical formulation are familiar to the person skilled in the art on the basis of his expert knowledge. Besides solvents, gel formers, suppository bases, tablet auxiliaries and other active compound excipients, antioxidants, dispersants, emulsifiers, antifoams, flavor enhancers, preservatives, solubilizers or colorants, for example, can be used.

For a form for oral administration, the active compounds are mixed with the additives suitable for this purpose, such as carriers, stabilizers or inert diluents, and brought by the customary methods into the suitable administration forms, such as tablets, coated tablets, hard gelatine capsules, or aqueous, alcoholic or oily solutions. Inert excipients which can be used are e.g. gum arabic, magnesia, magnesium carbonate, potassium phosphate, lactose, glucose or starch, in particular corn starch. In this connection, preparation can take place either as dry or moist granules. Suitable oily excipients or solvents are, for example, vegetable or animal oils, such as sunflower oil or cod liver oil.

For subcutaneous or intravenous administration, the active compounds, if desired with the substances customary for this purpose such as solubilizers, emulsifiers or other auxiliaries, are brought into solution, suspension or emulsion. Suitable solvents are e.g.: water, physiological saline solution or alcohols, e.g. ethanol, propanol, glycerol and also sugar solutions such as glucose or mannitol solutions, or alternatively a mixture of the various solvents mentioned.

Pharmaceutical formulations suitable for administration in the form of aerosols or sprays are e.g. solutions, suspensions or emulsions of the active compound of the formula I in a pharmaceutically acceptable solvent, such as, in particular, ethanol or water, or a mixture of such solvents.

If required, the formulation can also contain still other pharmaceutical auxiliaries such as surfactants, emulsifiers and stabilizers as well as a propellant. Such a preparation customarily contains the active compound in a concentration of about 0.1 to 10, in particular of about 0.3 to 3% by weight.

The dose of the active compound of the formula I to be administered and the frequency of administration depend on the potency and duration of action of the compounds used; additionally also on the nature and severity of the disease to be treated and on the sex, age, weight and individual responsiveness of the mammal to be treated.

On average, the daily dose of a compound of the formula I in the case of a patient of about 75 kg in weight is at least 0.001 mg/kg, preferably 0.01 mg/kg, to at most 10 mg/kg, preferably 1 mg/kg of body weight. In acute episodes of the illness, for example immediately after suffering a cardiac infarct, even higher and especially more frequent doses may be necessary, e.g. up to 4 individual doses per day. In particular when used i.v., for example in an infarct patient in the intensive care unit, up to 200 mg per day may be necessary.

List of abbreviations:

| | |
|---|---|
| MeOH | Methanol |
| DMF | N,N-dimethylformamide |
| RT | Room temperature |
| EA | Ethyl acetate (EtOAc) |
| m.p. | Melting point |
| THF | Tetrahydrofuran |
| eq. | Equivalent |

Experimental section

General procedure for the preparation of benzoylguanidine (I)

Variant A: from benzoic acids (II, L=OH)

1.0 eq. of the benzoic acid derivative of the formula II is dissolved or suspended in anhydrous THF (5 ml/mmol) and then treated with 1.1 eq. of carbonyldiimidazole. After stirring for 2 hours at RT, 5.0 eq. of guanidine are introduced into the reaction solution. After stirring overnight, the THF is distilled off under reduced pressure (rotary evaporator) the residue is treated with water and adjusted to pH 6 to 7 using 2N HCl and the corresponding benzoylguanidine (formula I) is filtered off. The benzoylguanidines thus obtained can be converted into the corresponding salts by treatment with aqueous, methanolic or ethereal hydrochloric acid or other pharmacologically tolerable acids.

General procedure for the preparation of benzoylguanidines (I)

Variant B: from alkyl benzoates (II, L =O-alkyl)

1.0 eq. of the alkyl benzoate of the formula II and 5.0 eq. of guanidine (free base) are dissolved in isopropanol or suspended in THF and heated to reflux (typical reaction time 2 to 5 h) until conversion is complete (thin-layer checking). The solvent is distilled off under reduced pressure (rotary evaporator), the residue is taken up in EA and the solution is washed 3×with NaHCO$_3$ solution. It is dried over Na$_2$SO$_4$, the solvent is distilled off in vacuo and the residue is chromatographed on silica gel using a suitable eluent, e.g. EA/MeOH 5:1. (For salt formation cf. variant A)

EXAMPLE 1

4-(2'-Fluoro-2'-propyl) benzoylguanidine hydrochloride:
Colorless crystals, m.p. 220° C.
Synthetic route:
a) Preparation of the Grignard compound of 4-chloro-α-methylstyrene by means of Rieke magnesium in THF under reflux and subsequent reaction with 0.95 equivalents of methyl chloroformate at RT. Aqueous working up, extraction with ethyl acetate and column chromatography using cyclohexane/ethyl acetate 85:15 affords methyl 4-isopropenylbenzoate as colorless crystals.
b) Methyl 4-(1'-bromo-2'-fluoroprop-2'-yl)benzoate from a) by reaction with 1.2 equivalents of N-bromosuccinimide in methylene chloride in the presence of 3 equivalents of triethylamine trihydrofluoride at −10° C. for 15 minutes and a further 60 minutes at RT. After aqueous working up and subsequent extraction followed by a purification by column chromatography using cyclohexane/ethyl acetate 7:3, colorless crystals, m.p. 79° C., are obtained.
c) Methyl 4-(2'-fluoro-2'-propyl)benzoate from b) by means of tributyltin hydride (addition of 1.6 equivalents twice in the course of 6 hours) in toluene at RT. After evaporation of the solvent and chromatography using n-heptane followed by n-heptane/ethyl acetate 4:1, a colorless oil is obtained.
d) 4-(2'-Fluoro-2'-propyl)benzoylguanidine hydrochloride from c) by guanylation according to variant B.

EXAMPLE 2

4-(2'-Trifluoromethylethyl)benzoylguanidine hydrochloride:
Colorless crystals, m.p. 168°–72° C.
Synthetic route:
a) Methyl 4-(2'-trifluoromethylethenyl)benzoate by coupling of the zinc chloride-transmetalated Grignard reagent of 2-bromo-2-trifluoromethylethene (3 equivalents) with methyl 4-bromobenzoate in THF under reflux, in the presence of 0.6 equivalents of palladium acetate and 0.1 equivalent of triphenylphosphine and 0.015 equivalent of copper(I) iodide. Aqueous working up and chromatography using n-heptane/ethyl acetate 4:1 yields a yellow oil.
b) Methyl 4-(2'-trifluoromethylethyl)benzoate from 2 a) by means of hydrogenation in the presence of palladium on active carbon in methanol in the course of 2 h. After removal of the solvent a colorless oil is obtained.
c) 4-(2'-Trifluoromethylethyl)benzoylguanidine hydrochloride from 2 b) according to variant B.

EXAMPLE 3

3-Methylsulfonyl-4-(2'-trifluoromethylethyl) benzoylguanidine hydrochloride:
Colorless crystals, m.p. 197° C.
Synthetic route:
a) Methyl 3-methylsulfonyl-4-(2'-trifluoromethylethenyl) benzoate analogously to 2 a) using methyl 4-bromo-3-methylsulfonylbenzoate as the coupling component.
Brownish wax after chromatography using n-heptane/ethyl acetate 3:2.
b) Methyl 3-methylsulfonyl-4-(2'-trifluoromethylethyl)-benzoate analogously to 2 b), colorless crystals, m.p. 128° C.
c) 3-Methylsulfonyl-4-(2'-trifluoromethylethyl) benzoylguanidine hydrochloride according to guanylation variant B.

We claim:

1. A benzoylguanidine selected from the group consisting of 4-(2'-trifluoromethylethyl) benzoylguanidine; 3-methylsulfonyl-4-(2'-trifluoromethylethyl) benzoylguanidine; or a pharmaceutically acceptable salt there of.

2. A pharmaceutical composition which comprises a compound as claimed in claim 1 together with a pharmaceutically acceptable carrier.

3. A method for the treatment of disorders induced by ischemia comprising administering to a host in need of said treatment an effective amount of a compound as claimed in claim 1.

* * * * *